US00PP31737P2

(12) United States Plant Patent
van Langen

(10) Patent No.: US PP31,737 P2
(45) Date of Patent: May 5, 2020

(54) ***PACHYVERIA* PLANT NAMED 'TSAECH1821'**

(50) Latin Name: **x*Pachyveria* hybrid**
Varietal Denomination: TSAECH1821

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 16/350,408

(22) Filed: Nov. 13, 2018

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
CPC ... A01H 5/12; A01H 5/02; A01H 5/00; A01H 6/32; A01H 6/00
See application file for complete search history.

(56) References Cited

U.S. PATENT DOCUMENTS

2019/0098822 P1 * 3/2019 van Langen ..... Plt./373

* cited by examiner

*Primary Examiner* — June Hwu
(74) *Attorney, Agent, or Firm* — Samuel R. McCoy, Jr.

(57) ABSTRACT

A new and distinct x*Pachyveria* plant named 'TSAECH1821' which is characterized by a relatively large plant size, strong foliage which is loosely held in a basal rosette, glaucous greyed-green foliage with a bluish hue, as well as the stability of these characteristics from generation to generation.

3 Drawing Sheets

Latin name of the genus and species: The Latin name of the genus and species of the novel variety disclosed herein is x*Pachyveria* hybrid.

Variety denomination: The inventive variety of x*Pachyveria* disclosed herein has been given the variety denomination 'TSAECH1821'.

BACKGROUND OF THE INVENTION

Parentage: 'TSAECH1821' is an intergeneric hybrid seedling selection resulting from the controlled pollination of an unnamed *Pachyphytum oviferum* x *Echeveria lauii* hybrid plant (not patented), the seed parent, with an unnamed *Echeveria lilacina* plant (not patented), the pollen parent. The crossing was made by the inventor in the autumn of 2013 at a commercial greenhouse in Heerhugowaard, the Netherlands. In the autumn of 2014, one seedling was observed which exhibited unique growth and foliage characteristics. The seedling was isolated for further evaluation in order to confirm the distinctness and stability of the characteristics first observed. Upon confirmation of distinctness and stability, 'TSAECH1821' was selected for commercialization in the winter of 2014.

Asexual Reproduction: Asexual reproduction of the new cultivar 'TSAECH1821', by way of rooting leaf cuttings, was first initiated in the summer of 2015 at the inventor's commercial greenhouse in Heerhugowaard, the Netherlands. Through five subsequent generations, the unique features of this cultivar have proven to be stable and true to type.

SUMMARY OF THE INVENTION

The cultivar 'TSAECH1821' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1821'. These characteristics in combination distinguish 'TSAECH1821' as a new and distinct x*Pachyveria* cultivar:

1. 'TSAECH1821' exhibits relatively large succulent foliage which is loosely held in a basal rosette; and
2. 'TSAECH1821' exhibits a relatively large plant size; and
3. 'TSAECH1821' exhibits thick, strong foliage; and
4. 'TSAECH1821' exhibits glaucous greyed-green foliage with a bluish hue.

BOTANICAL DESCRIPTION OF THE PLANT

Figure 1:
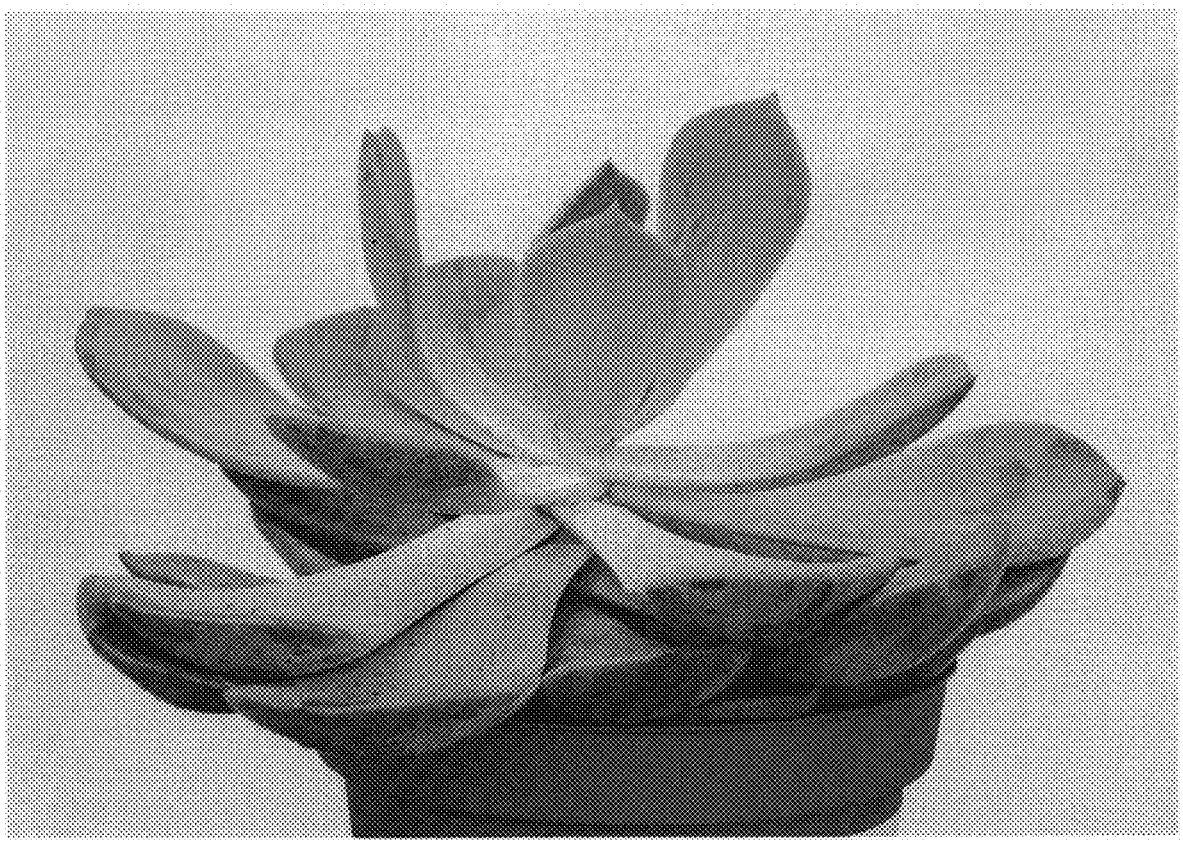
FIG. 1 illustrates, as nearly true as it is reasonably possible to make the same in color photographs of this type, an exemplary plant of 'TSAECH1821' grown in a commercial greenhouse in Heerhugowaard, the Netherlands. This plant is approximately 7 months old, shown planted in a 10 cm container.
Figure 2:
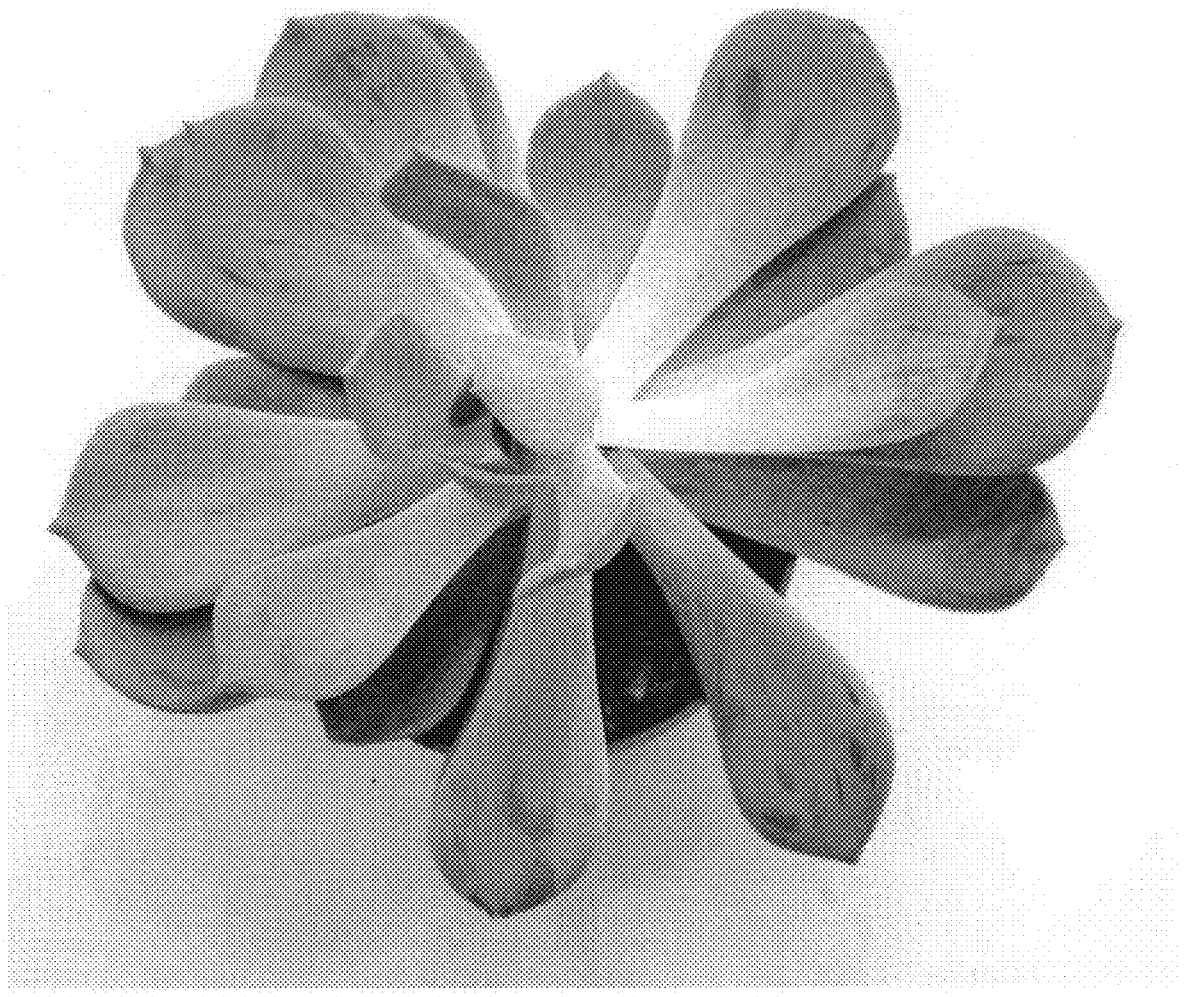
FIG. 2 illustrates, as nearly true as it is reasonably possible to make the same in color photographs of this type, the typical foliage arrangement of 'TSAECH1821'.
Figure 3:
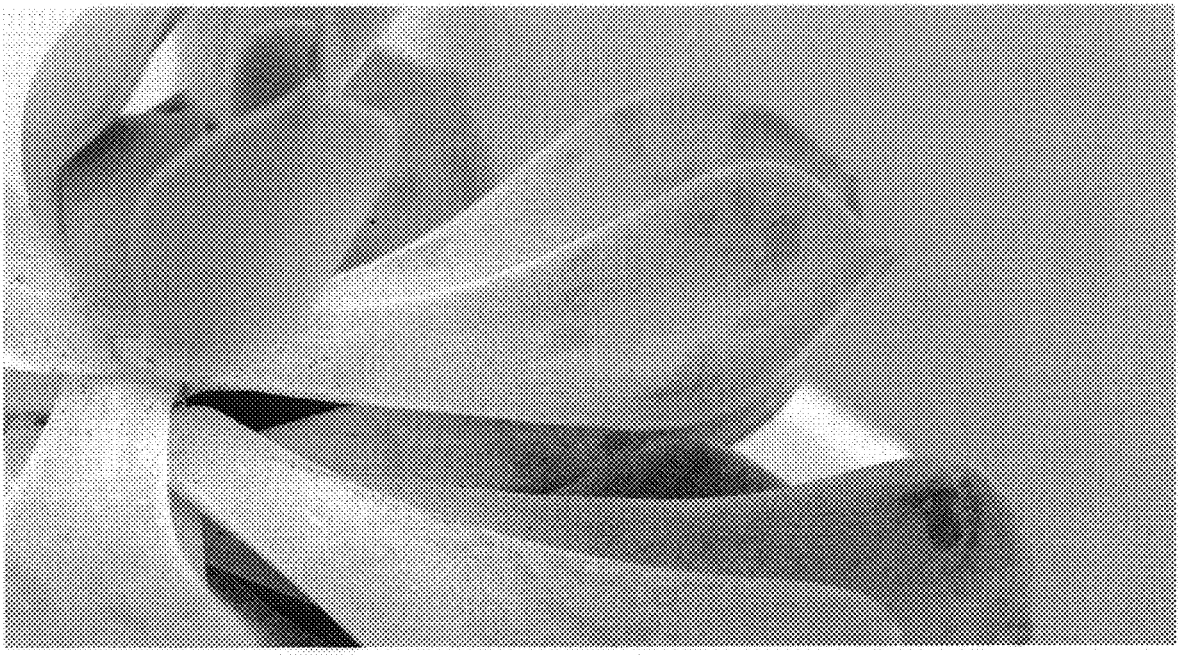
FIG. 3 illustrates, as nearly true as it is reasonably possible to make the same in color photographs of this type, the typical mature foliage of 'TSAECH1821'.

The following observations and measurements made in August of 2018 describe averages from a sample set of six specimens of 7 months old 'TSAECH1821' plants grown in 10 cm nursery containers at commercial greenhouse in Heerhugowaard, the Netherlands. Plants were produced using conventional greenhouse production protocols for *Echeveria* and *Pachyphytum* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1821' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'TSAECH1821' and comparisons with the parent plants and closest known comparator are provided below.

Plant description:

*Growth habit*.—Succulent perennial with foliage growing in a non-branched basal rosette.

*Plant shape*.—Flattened globular.

*Height from soil level to top of foliar plane*.—9.3 cm.

*Plant spread*.—Average of 20.0 cm.

*Growth rate*.—Moderate.

*Plant vigor*.—Moderate.

*Propagation*.—Type — Leaf cuttings. Time to initiate rooting — Approximately 21 days at 18 degrees Celsius. Crop time — Approximately 35 weeks to produce a marketable plant in an 11 cm container.

*Disease and pest resistance or susceptibility*.—Neither resistance nor susceptibility to typical *Echeveria* and *Pachyphytum* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a basal rosettes, eventually forming a short, unbranched stem with age; no lateral branching.

*Quantity of main stems*.—1.

*Main stem dimensions*.—4.3 cm long and 1.4 cm in diameter.

*Internode length*.—0.15 cm.

*Cross section*.—Rounded.

*Aspect*.—Nearly vertical.

*Strength*.—Moderately strong.

*Texture and luster*.—Glabrous and matte, due to a waxy layer covering the stem which is colored in between blue-green and greyed-green, nearest to RHS 122D and 188D.

*Color, when developing*.—Yellow-green, nearest to RHS 145D.

*Color of mature stem*.—Yellow-green, nearest to RHS 145D.

*Color at internodes*.—Yellow-green, nearest to RHS 145D.

Foliage:

*Arrangement*.—Rosette.

*Division*.—Simple.

*Attachment*.—Sessile.

*Quantity*.—Approximately 30 leaves per rosette.

*Shape*.—Spatulate to obovate.

*Dimensions*.—9.1 cm long, 3.9 cm wide, and 0.7 cm thick, on average.

*Aspect*.—Slightly concave and slightly curved upward.

*Attitude*.—Younger foliage near the center of the rosette is loosely held upward and outward; foliage becoming progressively more relaxed towards the outer whorl of the rosette, ultimately becoming near horizontal at the outer whorl of foliage.

*Apex*.—Apiculate.

*Base*.—Long cuneate.

*Margin*.—Entire; not undulated or lobed.

*Pubescence, texture and luster of the adaxial surface*.—Glabrous, smooth, and matte; moderately glaucous.

*Pubescence, texture and luster of the abaxial surface*.—Glabrous, smooth, and matte; moderately glaucous.

*Color*.—Juvenile foliage, adaxial surface — Greyed-green, nearest to RHS 191A, and fading lighter towards the base, nearest to RHS 193A; the epicuticular glaucous wax covering the leaf surface is greyed-green, nearest to a mixture of RHS 188A and 188B; tipped and narrowly margined with greyed-red towards the apex, nearest to a mixture of RHS 182C and 182D. Juvenile foliage, abaxial surface — Greyed-green, nearest to RHS 191B, and fading lighter towards the base, nearest to RHS 194C; the epicuticular glaucous wax covering the leaf surface is greyed-green, nearest to a mixture of RHS 188A and 188B; tipped and narrowly margined with greyed-red towards the apex, nearest to a mixture of RHS 182C and 182D. Mature foliage, adaxial surface — Greyed-green, nearest to RHS 189A, and fading lighter towards the base, nearest to RHS 193A; the epicuticular glaucous wax covering the leaf surface is greyed-green, nearest to a mixture of RHS 188A and 188B; tipped and narrowly margined with greyed-red towards the apex, nearest to RHS 181D. Mature foliage, abaxial surface — Greyed-green, nearest to RHS 191A, and fading lighter towards the base, nearest to RHS 193A; the epicuticular glaucous wax covering the leaf surface is greyed-green, nearest to a mixture of RHS 188A and 188B; tipped and narrowly margined with greyed-red towards the apex, nearest to RHS 181D.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

The seed parent, an unnamed *Pachyphytum oviferum* x *Echeveria lauii* hybrid plant (not patented), is no longer in cultivation or otherwise available, therefore a comparison is not possible.

Plants of the new cultivar 'TSAECH1821' differ from the pollen parent, an unnamed *Echeveria lilacina* plant (not patented), in the following characteristics described in Table 1 below.

TABLE 1

| Characteristic | 'TSAECH1821' | Pollen parent |
|---|---|---|
| Plant size. | Larger than the pollen parent. | Smaller than 'TSAECH1821'. |
| Growth habit. | Foliage loosely held in an irregular rosette. | Foliage tightly arranged in a symmetrical rosette. |
| Foliage abundance. | Less abundant. | More abundant. |
| Leaf apex. | Apiculate with a shorter, less prominent point, | Apiculate with a longer, more prominent point. |
| General coloration of the mature foliage. | Greyed-green with a bluish hue. | Appearing as a light blue-grey and heavily suffused with lilac. |

COMPARISONS WITH THE CLOSEST KNOWN COMPARATOR

Plants of the new cultivar 'TSAECH1821' differ from the closest known commercial comparator, x*Pachyveria* 'TSAECH1708' (U.S. patent application Ser. No. 16/350,122), in the following characteristics described in Table 2 below.

TABLE 2

| Chatacteristic | 'TSAECH1821' | 'TSAECH1708' |
|---|---|---|
| Plant size. | Larger than 'TSAECH1708'. | Smaller than 'TSAECH1821'. |
| Growth habit. | Foliage is loosely held in a basal rosette. | Foliage is tightly held in a basal rosette. |
| Abundance of foliage. | Less abundant. | More abundant. |
| Foliage size. | Larger than 'TSAECH1708' | Smaller than 'TSAECH 1821' |
| General coloration of the mature foliage. | Greyed-green with a bluish hue; tipped and narrowly margined pink. | Greyed-green with a pinkish hue. |

That which is claimed is:

1. A new and distinct variety of x*Pachyveria* hybrid plant named 'TSAECH1821', substantially as described and illustrated herein.

* * * * *